(12) United States Patent
Gray

(10) Patent No.: US 9,618,628 B2
(45) Date of Patent: Apr. 11, 2017

(54) RADIOLOGY DEVICE

(71) Applicant: AG MEDICAL, Saint-Aubin (FR)

(72) Inventor: David Gray, Antony (FR)

(73) Assignee: AG MEDICAL, Saint-Aubin (FR)

( * ) Notice: Subject to any disclaimer, the term of this patent is extended or adjusted under 35 U.S.C. 154(b) by 0 days.

(21) Appl. No.: 14/760,972

(22) PCT Filed: Jan. 16, 2014

(86) PCT No.: PCT/EP2014/050811
§ 371 (c)(1),
(2) Date: Jul. 14, 2015

(87) PCT Pub. No.: WO2014/114555
PCT Pub. Date: Jul. 31, 2014

(65) Prior Publication Data
US 2015/0346353 A1    Dec. 3, 2015

(30) Foreign Application Priority Data

Jan. 23, 2013 (FR) .................................. 13 50578

(51) Int. Cl.
*G01T 1/161* (2006.01)
*G01T 1/20* (2006.01)
(Continued)

(52) U.S. Cl.
CPC ............ *G01T 1/161* (2013.01); *A61B 6/4258* (2013.01); *A61B 6/4405* (2013.01); *G01T 1/175* (2013.01); *G01T 1/202* (2013.01)

(58) Field of Classification Search
CPC ..... A61B 6/4258; A61B 6/4405; G01T 1/161; G01T 1/175; G01T 1/202
See application file for complete search history.

(56) References Cited

U.S. PATENT DOCUMENTS

| 4,572,197 A | 2/1986 | Moore et al. |
| 4,682,604 A | 7/1987 | Fymat et al. |

(Continued)

FOREIGN PATENT DOCUMENTS

| DE | 2641039 | 3/1978 |
| WO | 2006038386 A1 | 4/2006 |

OTHER PUBLICATIONS

A. M. J. Jaspers, The Measurement of Radioactive Iodine in the Thyroid Gland, Philips Technical Review, 1956-57, 18-3, pp. 87-88.
(Continued)

*Primary Examiner* — Mark R Gaworecki
(74) *Attorney, Agent, or Firm* — Greer, Burns & Crain, Ltd.

(57) ABSTRACT

A radiology device includes at least one gamma radiation sensor, an acquisition device arranged to acquire data from each gamma radiation sensor, a transmission device arranged to transmit the acquired data outside the device, at least one battery arranged to store electrical energy and to electrically supply each sensor, the acquisition device and the transmission device. The radiology device is arranged to be carried entirely by the user. An application of the present radiology device is the treatment of cancers by administration of radionuclides.

8 Claims, 3 Drawing Sheets

(51) Int. Cl.
- *A61B 6/02* (2006.01)
- *G01T 1/202* (2006.01)
- *G01T 1/175* (2006.01)
- *A61B 6/00* (2006.01)

(56) References Cited

U.S. PATENT DOCUMENTS

| | | | |
|---|---|---|---|
| 5,647,363 A | 7/1997 | Rabito et al. | |
| 2004/0251419 A1* | 12/2004 | Nelson | G01T 1/243 250/370.09 |
| 2007/0208232 A1* | 9/2007 | Kovacs | A61B 5/02055 600/300 |

OTHER PUBLICATIONS

French Search Report from French Application No. 1350578, dated Sep. 13, 2013.
International Search Report from International Application No. PCT/EP2014/050811, dated May 8, 2014.

\* cited by examiner

RADIOLOGY DEVICE

BACKGROUND

The present invention relates to a radiology device.

Such a device allows a user to investigate a treatment of a patient emitting a high level of radioactivity without risk to the medical personnel or to other patients. The field of the invention is most particularly but non-limitatively that of cancer therapies by the administration of radionuclides.

A method of cancer treatment of a patient is to subject this patient to a high activity of a radioactive substance, by the administration of radionuclides, with the aim of reducing or eliminating the tumour cells.

In view of the high radioactivity of a patient subjected to such a treatment, there are then two possible options:
  Either to investigate the condition of the patient; in view of the high radioactivity of the patient, this poses a problem for the radiological protection on the one hand of the medical personnel in contact with the patient and on the other hand of the other patients likely to use the room containing the dedicated equipment (for example a PET scanner, for "positron emission tomography").
  Or to place the patient in an isolation room, isolating them from the medical personnel and from rooms which may be shared with other patients, until their radioactivity level falls below a certain threshold, which poses a problem for monitoring the treatment and the patient.

The purpose of the invention is to propose a device making it possible to solve these two problems.

SUMMARY

This objective is achieved with a radiology device comprising:
  at least one gamma radiation detector,
  acquisition means arranged in order to acquire data from each gamma radiation detector,
  transmission means arranged in order to transmit the acquired data to outside the device,
  at least one battery arranged in order to store electrical power and supply electricity to each detector, the acquisition means and the transmission means.

The device according to the invention is preferably arranged in order to be worn in its entirety by a user. As will be described hereinafter, this can be in particular due to its weight, and/or its range (battery, storage means for local recording and/or wireless transmission means, for example by Wifi), and/or the fact that it can be advantageously arranged so as not to require a wired connection to outside the device according to the invention during the acquisition by the acquisition means of data from at least one detector.

The transmission means:
  can comprise means for storing the data in the device. In this case, the transmission means also preferably comprise means for transmitting data to outside the device by a wired connection, arranged in order to transmit data after their acquisition by the acquisition means and their storage by the storage means; and/or
  can be arranged in order to send data to outside the device via a wireless link, preferably as they are acquired by the acquisition means.

The total weight of the device according to the invention can be less than four kilograms, preferably less than two kilograms, ideally less than one kilogram.

The device according to the invention can also comprise attachment means arranged in order to attach at least one of the detectors to a part of the user's body. The attachment means can comprise a neck brace for at least one of the detectors. The at least one detector can comprise a first group of two detectors placed:
  on a front face of the neck brace, this front face being intended to be positioned around a neck extending longitudinally along an axis of the neck and on the side of the anterior face of this neck, and
  preferably symmetrically with respect to a plane of symmetry so that the axis of the neck forms part of this plane of symmetry.

The at least one gamma radiation detector can comprise at least one first group (each detector of which is placed on the neck brace) and a second group (each detector of which is not placed on the neck brace and can be moved independently of the neck brace), each group comprising at least one gamma radiation detector, the attachment means not being common for the first group and the second group, so that:
  the attachment means comprise the neck brace for the first group, and
  the second group is arranged in order to act as a measurement reference for the first group.

The attachment means can comprise an article of clothing to hold at least one of the detectors.

The at least one gamma radiation detector can comprise at least two groups each comprising at least one gamma radiation detector so that the attachment means are not common for all the groups of detectors. The two groups can comprise a second group arranged in order to act as a measurement reference for the first group.

The device according to the invention preferably comprises gamma radiations detectors only, and no X-ray detector.

The acquisition means preferably comprise a dedicated electronic acquisition module for each gamma radiation detector and integral with this detector.

The transmission means and the at least one battery are preferably grouped together in a case electrically connected to each detector by a wired connection arranged in order to supply electricity to each detector by the at least one battery and in order to transfer data to the transmission means.

The device according to the invention can also comprise means for measuring a heart rate and/or means for measuring a respiration rate of the user and means for synchronizing the acquisition of data from each gamma radiation detector with the heart rate and/or the respiration rate.

BRIEF DESCRIPTION OF THE DRAWINGS

Other advantages and characteristics of the invention will become apparent on examination of the detailed description of implementations and embodiments which are in no way limitative, and of the attached diagrams, in which.

DETAILED DESCRIPTION

As these embodiments are in no way limitative, consideration may be given in particular to variants of the invention comprising only a selection of the characteristics described hereinafter in isolation from the other characteristics described (even if this selection is isolated within a sentence comprising these other characteristics), if this selection of characteristics is sufficient to confer a technical advantage or to differentiate the invention from the prior art. This selection comprises at least one characteristic preferably at least one functional characteristic without structural details, or with only a part of the structural details if this part alone is sufficient to confer a technical advantage or to differentiate the invention from the prior art.

Figure 1:
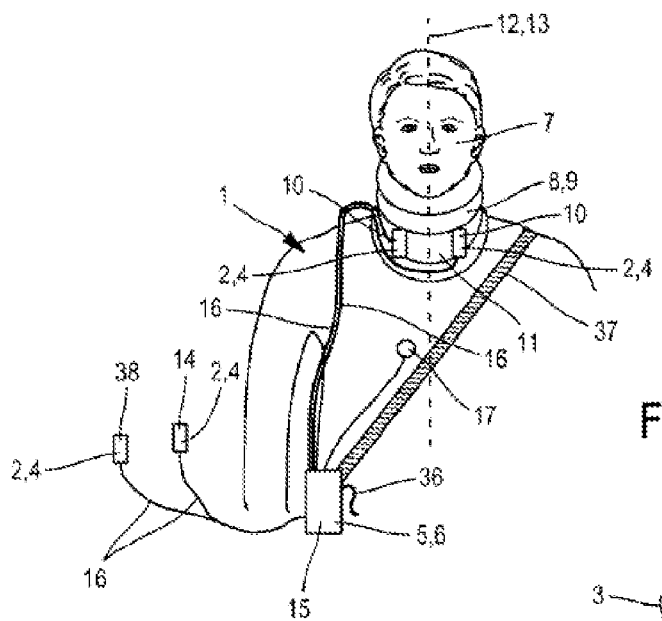
FIG. 1 shows a preferred embodiment of the device according to the invention worn by a human user 7 (also called the patient)
Figure 2:
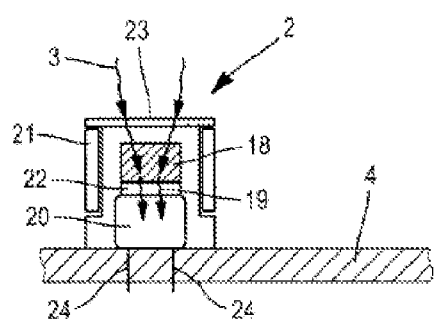
FIG. 2 shows a detector 2 of the device 1 according to the invention of FIG. 1, carried by its associated electronic acquisition module 4.
Figure 3:
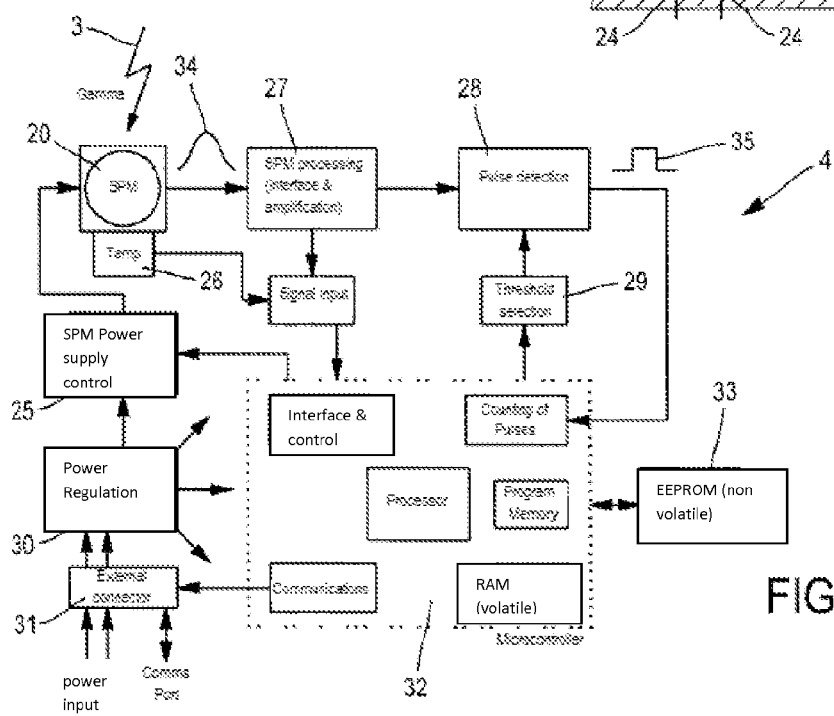
FIG. 3 shows an electronic acquisition module 4 of a detector 2 of the device 1 according to the invention of FIG. 1.
Figure 4:
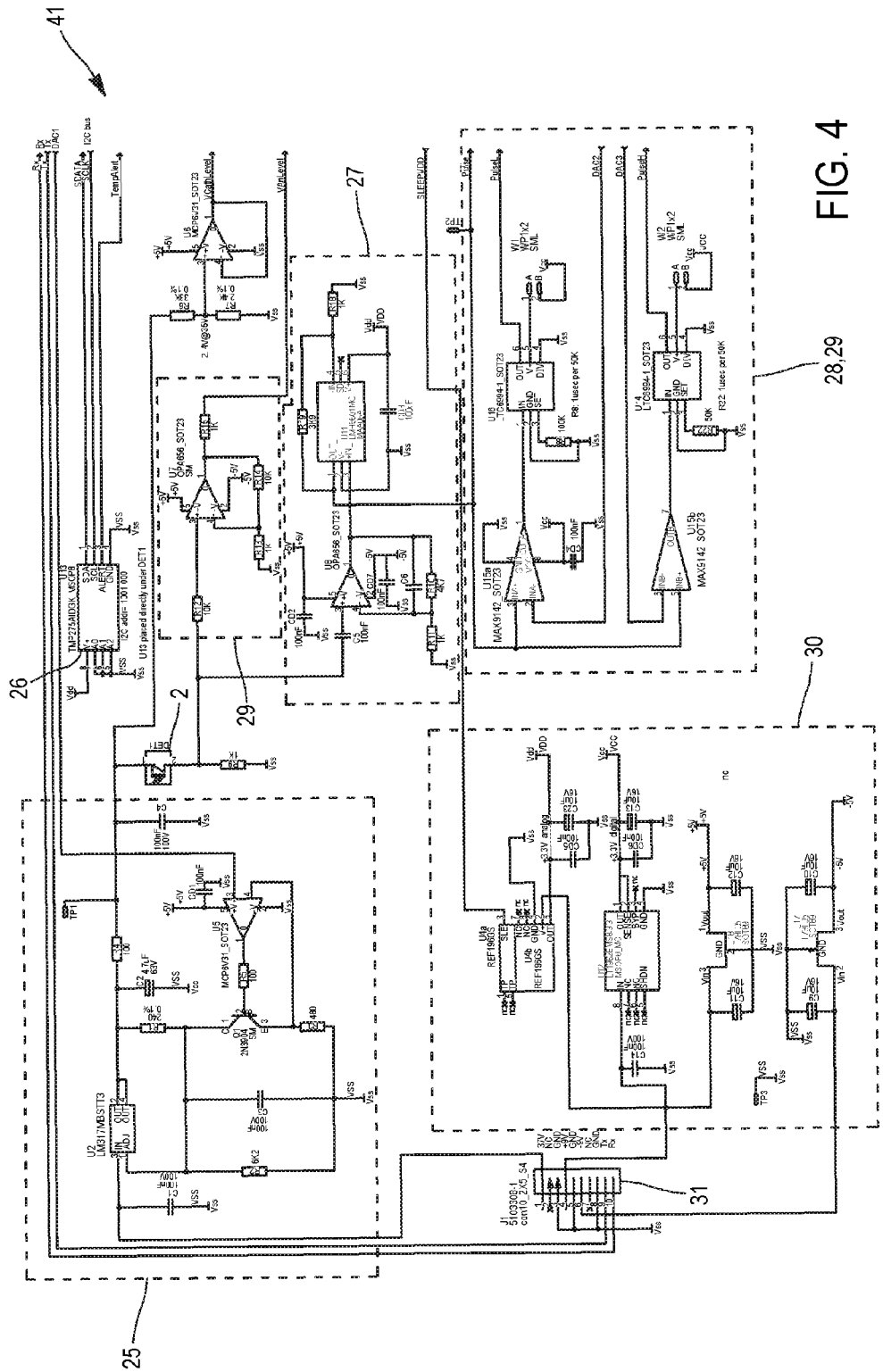
FIG. 4 shows in detail a first part 41 of an electronic acquisition module 4 of a detector 2 of the device 1 according to the invention of FIG. 1.
Figure 5:
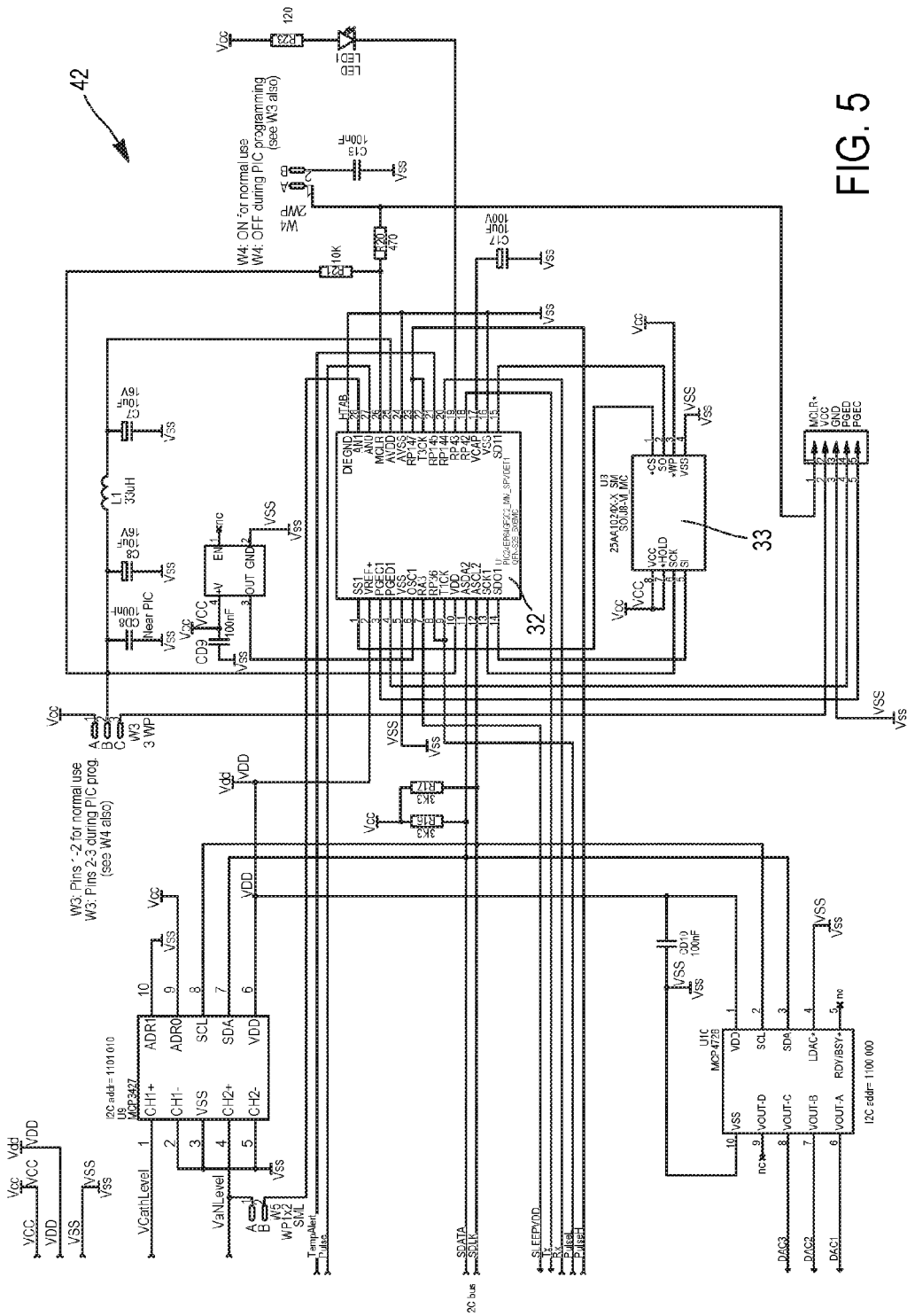
FIG. 5 shows in detail a second part 42 of an electronic acquisition module 4 of a detector 2 of the device 1 according to the invention of FIG. 1.

Firstly there will be described, with reference to FIGS. 1 to 5, a preferred embodiment of the radiology device 1 according to the invention.

By radiology is meant the use of a radioactive radiation for counting or dosimetry and/or for imaging.

The device 1 is a portable device, i.e. intended to be worn in its entirety by a user 7.

The device 1 comprises at least one detector 2 of gamma radiation 3. In the case of the device 1 shown in FIG. 1, this device 1 comprises four detectors 2.

By gamma radiation 3 is meant preferably electromagnetic radiation with a frequency greater than $7 \times 10^{18}$ Hertz, preferably comprised between $7 \times 10^{18}$ Hertz and $3 \times 10^{22}$ Hertz (or with a wavelength less than $10^{-11}$ metre, or comprised between $10^{-14}$ metre and $10^{-11}$ metre). Each detector is preferably arranged in order to detect gamma radiation having an energy comprised between 30 keV (Kiloelectron volts) and 600 keV, such as gamma radiation corresponding to Iodine 131 (364 keV).

In the case of the device 1, all the detectors 2 have the same technical characteristics described hereinafter. Each detector 2 is for example a detector with the reference AGM SPM Sensor SSL-CsI-001.

Each detector 2 of gamma radiation 3 comprises:
- a scintillation crystal 18 (for example of the CsI(TI) thallium-doped caesium-iodine type) arranged in order to convert gamma radiation 3 into at least one new photon 19 with a "visible" wavelength different from (preferably greater than) that of the photons of the gamma radiation 3 (these new photons 19 having a typical frequency comprised between $4.3 \times 10^{14}$ Hertz and $9.4 \times 10^{14}$ Hertz, or a wavelength comprised between 320 nanometres and 700 nanometres), and
- a detector or photomultiplier 20 (preferably of the SiPM (for Silicon Photomultiplier) type, for example with the reference SensL MicroSL30035-X13 or Hamamatsu S10931-050P) arranged in order to capture each new photon 19 originating from the crystal 18 and to generate, depending on the photons 19 captured, an electrical signal corresponding to a detection of the gamma radiation by the detector 2.

The crystal 18 and the photomultiplier 20 of each detector 2 are mounted inside a conduit of a collimator 21, preferably composed at least partially of aluminium and/or tungsten.

The crystal 18 and the photomultiplier 20 are optically connected and in contact with a layer of optical gel 22 (for example with the reference NyoGel OC-431A-LVP or OC-462 from Neyco), having the same optical index as the crystal 18.

The crystal 18 is preferably preceded by a filter 23 that allows only the gamma radiation 3 to pass from outside the device 1 to the crystal 18 (or at least, blocks the light with a wavelength "visible" to the photomultiplier 20)

The device 1 also comprises acquisition means 4, 41, 42 arranged in order to acquire data from each detector 2 of gamma radiation 3.

The acquisition means 4, 41, 42 comprise a dedicated electronic acquisition module 4 (typically an electronic board) for each gamma radiation detector 2 and firmly fixed to this detector 2.

The photomultiplier 20 of each detector 2 is mounted (by soldering the electrodes 24 of the photomultiplier 20 of this detector 2) onto the acquisition electronic board associated with this detector 2.

Within each acquisition electronics 4, an electronic processing module 27 (interface and amplification) is arranged in order to shape a signal 34 (of any shape, typically a curved pulse) generated by the detector 2 associated with this acquisition electronics 4. An electronic pulse detection module 28 is arranged in order to generate a pulse (typically a square pulse 35) if the signal 34, after processing by the module 27, exceeds a certain threshold. An electronic module 26 is arranged in order to measure the temperature of the photomultiplier 20. This module 26 comprises a temperature sensor with the reference Texas Instruments TMP275. An electronic module 29 for threshold selection is arranged in order to adjust this threshold, preferably as a function of the temperature measured by the module 26, and is arranged in order to be able to select only a part of the gamma radiation spectrum and in order to calibrate the detector 2. An electronic module 25 is arranged in order to control the electricity supply to the photomultiplier 20, preferably as a function of the temperature measured by the module 26. A microcontroller 32 (reference MicroChip PIC24EP64GP202) is arranged for overall control. The acquisition electronics 4 of the detector 2 also comprise a memory 33, typically of the EEPROM type (for Electrically-Erasable Programmable Read-Only Memory), for example with the reference MicroChip 25AA1024X), arranged in order to store the data acquired from this detector 2 via its associated electronic acquisition module 4. An electronic supply module 30 is arranged in order to distribute and regulate the electrical power for the whole of the acquisition electronics 4 of the detector 2. The acquisition electronics 4 of the detector also comprises a connector 31.

For each detector 2, the data thus acquired via the acquisition means (i.e. via the acquisition electronics 4 associated with this detector 2) typically comprise:
- preferably a gamma radiation measurement (for example number of pulses 35) per unit of time as a function of time (typically the detector 2 will count the number of pulses 35 per second over a duration of several seconds, preferably every N minutes, with N being an integer greater than or equal to 1) (for example several measurement points, each measurement point having a format of the type: 10 pulses 35 per second over a period of time T comprised between t=3 seconds and t=6 seconds, with a measurement point every 3 seconds or every minute), or
- a gamma radiation measurement (for example number of pulses 35) as a function of time (for example several measurement points, each measurement point being of a format of the type: 30 pulses 35 over a period of time T comprised between t=3 seconds and t=6 seconds; or even several measurement points, two successive measurement points being of a format of the type: $n^{th}$ pulse detected at t=3 seconds, $(n+1)^{th}$ pulse detected at t=3.1 seconds)

Each detector 2 and its associated acquisition electronics 4 are arranged so that together they convert a gamma radiation 3 into an electronic pulse 35. Each acquisition electronics 4 is arranged in order to count the number of gamma rays 3 that strikes the associated detector 2 preferably within a predetermined period of time T, and in order to store this figure (in the memory 33) for several consecutive periods. These data are then sent (via the connector 31) to a central board (electronic board of the transmission means 5).

The device 1 is arranged in order to be worn in its entirety by a user 7.

The device 1 is arranged in order not to require a wired connection from the device 1 to outside the device 1 during the acquisition of data from at least one detector 2 via acquisition means 4, 41, 42. Thus, the device 1 according to the invention makes it possible to monitor a patient 7 and their treatment, while allowing them to move freely and to live normally without any movement constraint. The patient no longer needs to be in a specific room (such as a PET scanner room) and can be placed in a room such as an isolation room for the safety of the medical personnel and the other patients.

The acquisition means 4, 41, 42 are preferably arranged for a continuous acquisition of dosimetric reading data of gamma radiation 3 over a period of time T, and for storing such an acquisition over several successive periods T. This makes it possible to establish how the patient 7 (typically their thyroid) reacts to the administration of the therapeutic radionuclides, preferably while the patient 7 remains in an isolation room. In addition to the protection of the medical personnel and the other patients, this allows a quantitative review of the absorption of the radionuclides by the patient 7 and this makes it possible to adjust the treatment accordingly.

The device 1 also comprises transmission means 5, arranged in order to transmit the acquired data to outside the device 1, and means 36, 37 for attaching the transmission means 5 to a part of the user's body 7.

The device 1 also comprises at least one battery 6 (for example 3 batteries in series, with the reference SAFT MP174565) arranged in order to store electrical power and to supply electricity to each detector 2, the acquisition means 4, 41, 42, and the transmission means 5, and means 36, 37 for attaching the at least one battery 6 to a part of the user's body 7. The at least one battery 6 is equipped with a plug making it possible to plug this at least one battery 6 into a cord connected to an electrical socket in order to recharge the battery occasionally, preferably when the device 1 is not being worn or used by a user 7 in order to acquire data from the gamma radiation detector 2.

The transmission means 5 and the at least one battery 6 are grouped together in a case 15 and electrically connected to each detector 2 (via the connector 31 of the acquisition electronics 4 associated with each detector 2) by a wired connection arranged in order to supply each detector 2 with electricity by the at least one battery 6 and for the transfer to the transmission means 5 of the data acquired from at least one detector 2 by the acquisition means 4. The case 15 is equipped with a shoulder strap 37 and/or a clip or loop 36 arranged in order to attach the case 15 to a belt of the user 7.

The transmission means 5 comprise storage means (a memory for example with the reference MicroChip 25AA1024X) arranged in order to store in the device 1 the data acquired from at least one detector 2 by the acquisition means 4.

The transmission means 5 comprise means (for example a USB port in order to connect the device 1 to a computer or a PC in order to retrieve the data and analyze them) in order to transmit these data to outside the device 1 by a wired connection, arranged in order to transmit these data after their acquisition by the acquisition means 4 and after their storage by the storage means. Thus, even when the patient 7 is in an isolation room, the medical personnel are protected from the radioactivity, but are still able to gain access at the end of the treatment to data describing the progress of the treatment over time, these data being much more complete than a simple photographic film badge dosimeter.

The transmission means 5 (typically comprising a Wifi transmitter) are arranged in order to send to outside the device 1 the data acquired from at least one detector 2 by the acquisition means 4 via a wireless link (for example of the Wifi type), preferably as they are acquired by the acquisition means 4, or even after their storage by the storage means. Thus, even when the patient 7 is in an isolation room, the medical personnel are protected from the radioactivity but are still able to monitor the treatment in another room, by means of the transmission means 5 arranged in order to send to outside the device 1 (preferably directly and not in deferred mode) via a wireless link (for example of the Wifi type) the data acquired from at least one detector 2 by the acquisition means 4.

The device 1 also comprises (preferably in the case 15) a processor arranged in order to monitor the state of charge of the at least one battery 6.

The device 1 also comprises attachment means 8 arranged in order to attach at least one of the detectors 2 to a part of the user's body 7. The attachment means 8 typically comprise means of tightening around this part of the body. It should be noted that these optional attachment means 8 are not necessarily present for all the detectors 2. The attachment means 8 are not common for all the detectors 2 but are preferably different, so that the at least one detector 2 of gamma radiation 3 comprises several groups 10, 14, 38 each comprising at least one gamma radiation detector 2, each group 10, 14, 38 being moveable with respect to the other groups.

In the device 1 the attachment means 8 comprise a neck brace 9 for a first group 10 of two detectors 2 intended for the acquisition of gamma radiation 3 originating from the thyroid of the user 7 (one detector 2 per lobe of the thyroid).

In a known manner, a neck brace (sometimes also called a cervical collar or cervical brace) is an appliance placed around the neck of the user 7 and arranged in order to maintain the head of the user 7 in a fixed position with respect to the neck of the user 7, this fixed position being generally straight and extended. A neck brace is thus equipped with means to immobilize the cervical vertebrae (and thus the neck) of the user 7.

A neck brace generally comprises a sternal support for user 7 and/or a mandibular support for user 7.

The two detectors 2 of the first group 10 are placed:
on or in a front face 11 of the neck brace 9 (on an inner or outer wall of the neck brace, or inside the neck brace) this front face 11 being intended to be positioned:
around the neck of the user 7, this neck extending longitudinally along an axis 12 of the neck, and on the side of the anterior face of this neck, and symmetrically with respect to a plane of symmetry 13 (perpendicular to the plane of FIG. 1) so that the axis 12 of the neck forms part of this plane of symmetry 13.

A second group 14 (in which each detector is not placed on the neck brace and can be moved independently of the neck brace) comprising a single detector 2 is arranged in order to act as a measurement reference for the first group 10, i.e. in order to measure the ambient radiation level of the environment of the user. It should be noted that this second group 14 is not equipped with attachment means 8.

A third group 38 comprising a detector 2 makes it possible to take measurements on another part of the body for example on the bladder of the patient 7. The part of the attachment means 8 (not shown) for this third group 38 comprises for example a self-adhesive surface or a Velcro fastening or a clip or a belt buckle, or an item of clothing (belt, jacket, sleeve, sleeveless jacket, shorts, helmet, hat, trousers, sock, shoe, glove, etc.) arranged (for example using a pocket) for holding a detector 2.

Optionally, the device 1 also comprises the following elements (not shown on the figures):

firstly:
  at least one system for measuring a heart rate of the user 7. Typically, each system for measuring a heart rate comprises an ECG (electrocardiogram) for example with the reference Lead Lok A10. Each detector 2 is equipped with its own system for measuring a heart rate directly connected to the acquisition electronics 4 of this detector 2 without passing via the case 15 of the battery 6 and of the transmission means 5, and/or
  at least one system 17 for measuring a respiration rate of the user 7. Typically, each system for measuring a respiratory rate comprises a piezoelectric pressure measurement system, for example with the reference Respironics CT2 P1823. The device 1 comprises a single respiratory rate measurement system 17, common to all the detectors 2, and preferably electrically connected to each detector 2 by passing via the case 15 of the at least one battery 6 and of the transmission means 5.
and also electronic means (inside each acquisition electronics 4) for synchronizing the acquisition of the data from each detector 2 of gamma radiation 3 with the heart rate and/or the respiratory rate.

This makes it possible to improve the accuracy of the data acquired by suppressing certain measurement artefacts.

The device 1 has a weight of less than one kilogram.

It should be noted that the device 1 comprises gamma radiation detectors only, and no X-ray detector.

Of course, the invention is not limited to the examples which have just been described, and numerous adjustments can be made to these examples without exceeding the scope of the invention.

In particular, variants of the device 1 can be envisaged, that may be combined with one another:
  the at least one detector 2 can comprise a single detector 2, or a single group 10, 14 or 38 of detectors,
  the attachment means 8 can be absent; in this case, each detector 2 can be fixed in a pocket that does not form part of the device 1 or by means of an adhesive tape or self-adhesive sticker or glue not forming part of the device 1,
  the means 36, 37 for attaching the at least one battery 6 and/or for attaching the transmission means 5 can be absent; in this case, the at least one battery 6 and/or the transmission means 5 can be attached in a pocket that does not form part of the device 1 or by means of an adhesive tape or self-adhesive sticker or glue not forming part of the device 1,
  at least one of the detectors 2 can comprise several pixels (for example one or more detectors with the reference SensL ArraySM-4), making it possible to carry out imaging (for example of the thyroid in the case of the neck brace), the acquired data even allowing imaging to be carried out as a function of time. The data acquired from this at least one of the detectors allow an image to be constructed. To this end, the device according to the invention comprises (preferably in the case 5 or in the electronics 5 of this at least one of the detectors) means (dedicated electronic circuit) for processing the acquired data and constructing an image in the form of electronic and/or computer data.

Of course, the different characteristics, forms, variants and embodiments of the invention can be combined with one another in various combinations to the extent that they are not mutually incompatible or exclusive. In particular, all the variants and embodiments previously described can be combined together.

The invention claimed is:

1. A radiology device for dosimetry, comprising:
at least one detector of gamma radiation comprising at least one first group and at least one second group, each of said at least one first group and each of said at least one second group comprising at least one gamma radiation detector;
acquisition means arranged for acquiring dosimetric reading data from each gamma radiation detector;
transmission means arranged for transmitting the acquired data to outside the device;
at least one battery arranged for storing electrical power and supply electricity to each detector, to the acquisition means and to the transmission means;
said device also comprising attachment means arranged for attaching at least one of the detectors to a part of the user's body;
wherein the attachment means are arranged for acquiring from each gamma detector:
a gamma radiation measurement per unit of time as a function of time, or
a gamma radiation measurement as a function of time;
the device being made to be worn in its entirety by a user and its weight being less than one kilogram;
the acquisition means comprising a dedicated electronic acquisition module for each gamma radiation detector and integral with this detector;
the attachment means comprising a neck brace for the first group;
the first group comprising two detectors placed on a front face of the neck brace, symmetrically with respect to a plane of symmetry;
the second group being arranged for acting as a measurement reference for the first group.

2. The device according to claim 1, wherein the second group is not carried by the neck brace.

3. The device according to claim 1, wherein the transmission means are arranged for sending data to outside the device by a wireless link.

4. The device according to claim 1, wherein the transmission means comprise means for storing the data in the device.

5. The device according to claim 4, wherein the transmission means comprise means for transmitting data to outside the device by a wired connection, arranged for transmitting data after the acquisition of the data by the acquisition means and storage of the data by the storage means.

6. The device according to claim 1, wherein the attachment means comprise an item of clothing arranged to hold at least one of the detectors.

7. The device according to claim 1, wherein the transmission means and the at least one battery are grouped together in a case electrically connected to each detector by a wired connection arranged for supplying electricity to each detector via the at least one battery and for transferring data to the transmission means.

8. The device according to claim 1, further comprising at least one of means for measuring a heart rate and means for measuring a respiration rate of the user and means for synchronizing the acquisition of data from each gamma radiation detector with the heart rate and/or the respiration rate.

* * * * *